United States Patent [19]

Demmering

[11] Patent Number: 5,399,792
[45] Date of Patent: Mar. 21, 1995

[54] PROCESS FOR THE PRODUCTION OF UNSATURATED FATTY ALCOHOLS

[75] Inventor: Guenther Demmering, Solingen, Germany

[73] Assignee: Henkel Kommanditgesellschaft auf Aktien, Duesseldorf, Germany

[21] Appl. No.: 204,251

[22] PCT Filed: Aug. 28, 1992

[86] PCT No.: PCT/EP92/01985

§ 371 Date: May 6, 1994

§ 102(e) Date: May 6, 1994

[87] PCT Pub. No.: WO93/05003

PCT Pub. Date: Mar. 18, 1993

[30] Foreign Application Priority Data

Sep. 6, 1991 [DE] Germany .................. 41 29 622.2

[51] Int. Cl.⁶ .................. C07C 31/20; C07C 33/02; C07C 33/025
[52] U.S. Cl. .................. 568/864; 568/885
[58] Field of Search .................. 568/885, 864

[56] References Cited

U.S. PATENT DOCUMENTS

| | | | |
|---|---|---|---|
| 2,322,095 | 6/1943 | Schmidt | 568/885 |
| 2,876,265 | 3/1959 | Braconier et al. | 568/885 |
| 3,729,520 | 4/1973 | Rutzen et al. | 260/638 A |
| 4,855,273 | 8/1989 | Pohl et al. | 502/244 |
| 4,982,020 | 1/1991 | Carduck et al. | 568/864 |
| 5,120,885 | 6/1992 | Tsukada et al. | 568/885 |
| 5,233,099 | 8/1993 | Tabata et al. | 568/885 |

FOREIGN PATENT DOCUMENTS

| | | |
|---|---|---|
| 0254189 | 1/1988 | European Pat. Off. |
| 0280982 | 9/1988 | European Pat. Off. |
| 1228603 | 11/1966 | Germany. |
| 2513377 | 9/1976 | Germany. |

*Primary Examiner*—Joseph E. Evans
*Attorney, Agent, or Firm*—Ernest G. Szoke; Wayne C. Jaeschke; John E. Drach

[57] ABSTRACT

Unsaturated fatty alcohols with 6 to 22 C atoms can be produced by directly hydrating deacidified and/or non-deacidified glyceride oils containing monounsaturated and/or polyunsaturated, straight chain and/or branched-chain fatty acids having 6 to 22 C atoms in the fatty acid residue, by applying a 30 to 100-fold excess of hydrogen in a pressure range from 50 to 300 bars, at temperatures from 200° to 400° C., to zinc-chrome-catalysts of the spinel type, while largely preserving the olefinic double bonds and with formation of propane and 1,2-propylene glycol.

11 Claims, No Drawings

PROCESS FOR THE PRODUCTION OF UNSATURATED FATTY ALCOHOLS

BACKGROUND OF THE INVENTION

This invention relates to a process for the production of unsaturated fatty alcohols by hydrogenation of deacidified and/or non-deacidified glyceride oils in the presence of zinc-chromium catalysts with formation of propane and 1,2-propylene glycol, the olefinic double bonds present in the starting material remaining largely intact.

STATEMENT OF RELATED ART

DE 25 13 377 B1 describes a process for the production of monounsaturated relatively high molecular weight fatty alcohols by catalytic hydrogenation of free, unsaturated fatty acids of relatively high molecular weight or esters thereof formed with monohydric alcohols of low molecular weight. The hydrogenation reaction is carried out on particulate zinc-containing catalysts of relatively low activity with no further addition of lower alcohols as diluents.

The readily volatile fatty acid methyl esters of unsaturated fatty acids are normally obtained from glyceride oils by transesterification with methanol.

Accordingly, the problem addressed by the present invention was to provide a process for the direct hydrogenation of the triglycerides, in which the transesterification step, i.e. the formation of methyl esters from the glyceride oils, would be eliminated.

DESCRIPTION OF THE INVENTION

The present invention relates to a process for the production of unsaturated fatty alcohols containing 6 to 22 carbon atoms, characterized in that deacidified and/or non-deacidified glyceride oils containing monounsaturated and/or polyunsaturated, predominantly linear and/or branched fatty acids containing 6 to 22 carbon atoms in the fatty acid residue are directly hydrogenated with a 30- to 100-fold excess of hydrogen on zinc-chromium catalysts of the spinel type under pressures of 50 to 300 bar and at temperatures of 200 to 350° C. with formation of propane and 1,2-propylene glycol, the olefinic bonds remaining largely intact.

It is only in exceptional cases that commercial catalysts for the hydrogenation of unsaturated fatty acid methyl esters to unsaturated fatty alcohols are also suitable for the hydrogenation of non-deacidified glyceride oils. However, it has surprisingly been found that the zinc-chromium catalysts to be used in accordance with the invention also show excellent activity in the hydrogenation of glyceride oils having acid values of 0 to 10. According to the present invention, the hydrogenation reaction can be controlled through the choice of the reaction temperature and the additions of catalyst in such a way that hardly any glycerol and only a little propane-1,2-diol are formed in the production of the fatty alcohols, propane instead being predominantly formed as a cleavage product.

The catalyst is used in particulate form, i.e. in the form of pellets, extrudate or granules.

One preferred embodiment of the present invention is characterized by the use of glyceride oils obtained from olive oil, rapeseed oils poor and rich in erucic acid, fish oil, beef tallow and/or lard.

The selectivity of the reaction in regard to alcohol formation and also in regard to maintenance of the double bonds and the cis-configuration of the starting oil is very high in the process according to the invention. The selectivity of the catalyst can be increased by suitable additional doping agents and additives.

In one embodiment of the invention, zinc-chromium catalysts doped with aluminium, manganese, cadmium and/or vanadium are used. In one preferred embodiment, zinc-chromium catalysts containing 1 to 8% by weight and preferably 1.5 to 5% by weight of the doping agents mentioned above, based on the weight of the catalyst, are used. The selectivity of the catalyst can be further increased by this measure.

In another preferred embodiment of the invention, zinc-chromium catalysts additionally doped with additions of barium and alkali metals are used. According to the invention, zinc-chromium catalysts containing 0.1 to 3% by weight and preferably 0.5 to 2% by weight of barium and/or alkali metals, more particularly potassium (based on the weight of the catalyst) are used. The long life of the catalyst is further improved by the additions of barium and small quantities of alkali metal.

In addition to the constituents mentioned above, catalysts used in accordance with the invention may contain typical binders. Another embodiment of the invention is characterized in that 1 to 4% by weight of graphite is added to the catalysts used in accordance with the invention to improve the processability of the granules and/or extrudates.

The following Examples are intended to illustrate the invention without limiting it in any way.

EXAMPLES

Example 1

In a kneader, 50 g of powder-form zinc oxide were mixed with 5 l of water and continuously kneaded with a solution of 35 kg of chromium trioxide in 30 l of water and 2 kg of 50% potassium hydroxide solution. 3% of graphite was added to the mixture obtained which was then dried and made into pellets 4 mm thick and 6 mm in diameter.

1.5 Liters of the catalyst pellets obtained were introduced into the tube reactor (diameter 42 mm; length 1,500 mm) of a continuous hydrogenation apparatus. The catalyst was reduced with hydrogen, the temperature being gradually increased from 180 to 400° C.

After the reduction, rapeseed oil poor in erucic acid (saponification value 190; iodine value 114; acid value 4) was introduced into the hydrogenation apparatus at a rate of 300 ml per hour and hydrogenated with hydrogen at a reaction temperature of 290° C. and under a pressure of 200 bar. The crude reaction product contained 2% by weight of 1,2-propylene glycol. After separation of the water of reaction and the 1,2-propylene glycol formed, the fatty alcohol mixture obtained had the following characteristic values:

Saponification value (SV): 206

Iodine value (IV): 180

Acid value (AV): 0.1

In Table 1 below, the composition of the fatty acid component of the rapeseed oil used as starting material (as determined on rapeseed oil methyl ester) is compared with the composition of the fatty alcohol mixture obtained.

TABLE 1

| | Composition - rapeseed oil and fatty alcohol mixture | |
|---|---|---|
| Chain length | Rapeseed oil % by weight | Fatty alcohol % by weight |
| C 16 saturated | 4.6 | 4.7 |
| C 18 saturated | 1.5 | 3.8 |
| C 18 monounsaturated | 60.0 | 70.1 |
| C 18 diunsaturated | 21.0 | 11.5 |
| C 18 triunsaturated | 9.5 | 6.3 |
| C 20 saturated | 3.4 | 3.3 |
| Hydrocarbons | — | 0.4 |

Example 2

Olive oil (saponification value 180, iodine value 85.6, acid value 6.7; 94% by weight cis components, 6% by weight trans components) was hydrogenated under the same conditions as in Example 1 using the catalyst described therein. The fatty alcohol mixture remaining after removal of the water of reaction and propanediol had the following characteristic data: SV 0.3, IV 87, 0.04; 90% cis components; 10% trans components.

The composition of the fatty acid component of the olive oil used as starting material and the composition of the fatty alcohol mixture obtained therefrom are shown in Table 2 below.

TABLE 2

| | Composition - olive oil and fatty alcohol mixture | |
|---|---|---|
| Chain length | Olive oil % by weight | Fatty alcohol % by weight |
| C 16 saturated | 16.3 | 16.0 |
| C 16 monounsaturated | 1.7 | 1.4 |
| C 18 saturated | 2.3 | 3.3 |
| C 18 monounsaturated | 61.8 | 67.0 |
| C 18 diunsaturated | 16.5 | 10.8 |
| C 18 triunsaturated | 0.7 | 0.4 |
| C 20 saturated | 0.7 | 0.6 |
| Hydrocarbons | — | 0.5 |

Example 3

8 Liters of the catalyst pellets described in Example 1 were reduced with hydrogen in the tube reactor (diameter 42 mm; length 6,000 mm) of a continuous hydrogenation apparatus first at 180° C. and then at 400° C. Hydrogen and rapeseed oil poor in erucic acid (AV 0.6, SV 191, IV 111) were passed over the reduced catalyst in co-current at 250 bar/310° C. The oil was introduced at a rate of 2 liters per hour corresponding to an lhsv of 2 $l^{-1}h^{-1}$. After removal of the water of reaction and the 1,2-propylene glycol formed, the fatty alcohol mixture obtained had the following characteristic data: AV 0.05, SV 1.0, IV 105, OHV 208.

In Table 3 below, the composition of the fatty acid component of the rapeseed oil low in erucic acid used as starting material (as determined on rapeseed oil methyl ester) is compared with the composition of the fatty alcohol mixture obtained.

TABLE 3

| | Composition - rapeseed oil and fatty alcohol mixture | |
|---|---|---|
| Chain length | Rapeseed oil % by weight | Fatty alcohol % by weight |
| C 18 saturated | 4.9 | 5.0 |
| C 18 saturated | 1.5 | 3.5 |
| C 18 monounsaturated | 60.0 | 64.5 |
| C 18 diunsaturated | 20.8 | 17.0 |
| C 18 triunsaturated | 9.3 | 6.0 |
| C 18 saturated | 3.4 | 3.5 |

TABLE 3-continued

| | Composition - rapeseed oil and fatty alcohol mixture | |
|---|---|---|
| Chain length | Rapeseed oil % by weight | Fatty alcohol % by weight |
| Hydrocarbons | — | 0.5 |

Example 4

Rapeseed oil rich in erucic acid (AV 7.8, SV 170, IV 102) was hydrogenated under the conditions described in Example 3 to form a fatty alcohol mixture having the following characteristic data: AV 0.02, SV 1.0, IV 99, OHV 182.

The composition of the fatty acid component of the rapeseed oil used as starting material and the composition of the fatty alcohol mixture obtained therefrom are shown in Table 4 below.

TABLE 4

| | Composition - rapeseed oil and fatty alcohol mixture | |
|---|---|---|
| Chain length | Rapeseed oil % by weight | Fatty alcohol % by weight |
| C 18 saturated | 3.7 | 3.8 |
| C 18 saturated | 0.9 | 3.6 |
| C 18 monounsaturated | 12.9 | 15.2 |
| C 18 diunsaturated | 14.1 | 10.8 |
| C 18 triunsaturated | 8.9 | 6.7 |
| C 18 saturated | 12.1 | 12.4 |
| C 22 unsaturated | 47.4 | 50.8 |
| Hydrocarbons | — | 0.3 |

Example 5

Palm oil (AV 7.4, SV 194, IV 50.6) was hydrogenated under the conditions described in Example 3 to form a fatty alcohol mixture having the following characteristic data: AV 0.1, SV 1.0, IV 50.4, OHV 214.

In Table 5 below, the composition of the fatty acid component of the palm oil used as starting material (as determined on palm oil methyl ester) is compared with the composition of the fatty alcohol mixture obtained.

TABLE 5

| | Composition - palm oil and fatty alcohol mixture | |
|---|---|---|
| Chain length | Palm oil % by weight | Fatty alcohol % by weight |
| C 16 | 3.0 | 3.0 |
| C 16 | 45.4 | 45.8 |
| C 18 saturated | 4.1 | 5.2 |
| C 18 monounsaturated | 38.0 | 38.8 |
| C 18 diunsaturated | 8.4 | 6.3 |
| C 18 triunsaturated | 0.3 | 0.3 |
| C 20 | 0.7 | 0.8 |

Example 6

Lard (AV 0.6, SV 192.3, IV 60.2) was hydrogenated under the conditions described in Example 3 to form a fatty alcohol mixture having the following characteristic data: AV 0.05, SV 1.0, IV 60.4, OHV 211.

In Table 6 below, the composition of the fatty acid component of the lard used as starting material (as determined on the methyl ester after transesterification) is compared with the composition of the fatty alcohol mixture obtained.

TABLE 6

| Composition - lard and fatty alcohol mixture | | |
|---|---|---|
| Chain length | Lard % by weight | Fatty alcohol % by weight |
| C 16 saturated | 1.7 | 1.8 |
| C 16 saturated | 25.1 | 26.8 |
| C 16 monounsaturated | 2.3 | 1.9 |
| C 18 saturated | 15.6 | 17.5 |
| C 18 monounsaturated | 43.2 | 45.8 |
| C 18 diunsaturated | 8.7 | 3.7 |
| C 18 triunsaturated | 0.7 | 0.6 |
| C 18 saturated | 2.5 | 2.4 |
| Hydrocarbons | — | 1.1 |

In Examples 3 to 6, approximately 80% of the theoretically expected quantity of 1,2-propylene glycol was hydrogenated to propane.

The catalyst depreciation, based on the oil throughput, amounted to 0.1%. Comparable results were obtained when tallow oil and butter fat were hydrogenated under the conditions of Example 3.

I claim:

1. A process for the production of an unsaturated fatty alcohol having from about 6 to about 22 carbon atoms which comprises contacting a deacidified or non-deacidified glyceride oil the fatty acid portions of which are at least monounsaturated and which have from above 6 to about 22 carbon atoms with from about 30 to about 100 molar excess of hydrogen in the presence of a zinc-chromium catalyst of the spinel type under a pressure of from about 50 to about 300 bar and at a temperature of from about 200° C. to about 400° C. to form said fatty alcohol, 1,2-propylene glycol, and propane; wherein the olefinic bonds of said fatty alcohol remain substantially unaffected.

2. The process of claim 1 wherein said glyceride oil is selected from the group consisting of olive oil, rapeseed oil rich in erucic acid, rapeseed oil low in erucic acid, fish oil, beef tallow, lard, and combinations thereof.

3. The process of claim 1 wherein said catalyst is doped with a metal selected from the group consisting of aluminum, cadmium, vanadium, and combinations thereof.

4. The process of claim 1 wherein said catalyst is doped with from about 1% to about 8% by weight of a metal selected from the group consisting of aluminum, cadmium, vanadium, and combinations thereof.

5. The process of claim 3 wherein said catalyst is further doped with barium or an alkali metal.

6. The process of claim 5 wherein said alkali metal is potassium.

7. The process of claim 3 wherein said catalyst is further doped with from about 0.1% to about 3% by weight of barium or an alkali metal.

8. The process of claim 4 wherein said catalyst is further doped with from about 1% to about 4% by weight of graphite.

9. The process of claim 5 wherein said catalyst is further doped with from about 1% to about 4% by weight of graphite.

10. The process of claim 6 wherein said catalyst is further doped with from about 1% to about 4% by weight of graphite.

11. The process of claim 7 wherein said catalyst is further doped with from about 1% to about 4% by weight of graphite.

* * * * *